(12) United States Patent
Kellie

(10) Patent No.: US 7,151,603 B2
(45) Date of Patent: Dec. 19, 2006

(54) OVERHEAD TRANSPARENCY CLARITY SIMULATOR

(75) Inventor: Truman F. Kellie, Lakeland, MN (US)

(73) Assignee: Samsung Electronics Co. Ltd., Suwon (KR)

( * ) Notice: Subject to any disclaimer, the term of this patent is extended or adjusted under 35 U.S.C. 154(b) by 285 days.

(21) Appl. No.: 10/837,036

(22) Filed: Apr. 30, 2004

(65) Prior Publication Data

US 2005/0243311 A1    Nov. 3, 2005

(51) Int. Cl.
*G01N 21/00* (2006.01)

(52) U.S. Cl. .................. 356/342; 356/239.1; 356/433; 356/443

(58) Field of Classification Search ............... 356/443, 356/432, 239.1, 239.2, 239.4, 239.5, 239.7, 356/239.8, 341, 444, 389, 433; 399/130; 250/559.02
See application file for complete search history.

(56) References Cited

U.S. PATENT DOCUMENTS

| | | | | |
|---|---|---|---|---|
| 3,361,029 A | * | 1/1968 | Russell et al. ............... 356/444 |
| 4,298,309 A | | 11/1981 | Stoltz ....................... 414/746.5 |
| 5,115,277 A | | 5/1992 | Camis ........................ 399/390 |
| 5,132,627 A | | 7/1992 | Popovic et al. ............. 324/452 |
| 5,176,974 A | | 1/1993 | Till et al. ...................... 430/42 |
| 5,208,093 A | | 5/1993 | Carls et al. ............... 428/195.1 |
| 5,302,439 A | | 4/1994 | Malhotra et al. ......... 428/32.28 |
| 5,410,392 A | | 4/1995 | Landa ......................... 399/308 |
| 5,451,458 A | * | 9/1995 | Malhotra ................. 428/32.28 |
| 5,519,479 A | | 5/1996 | Shimizu et al. ............. 399/333 |
| 5,543,177 A | | 8/1996 | Morrison et al. ........... 427/288 |
| 5,635,325 A | | 6/1997 | Inaba et al. ............. 430/108.4 |
| 5,790,255 A | | 8/1998 | Jackson et al. ............. 356/622 |
| 5,824,442 A | | 10/1998 | Tanikawa et al. ............. 430/45 |
| 5,824,800 A | * | 10/1998 | Tamura et al. .............. 540/142 |
| 5,916,718 A | | 6/1999 | Kellie et al. ................... 430/45 |
| 6,055,391 A | | 4/2000 | Jackson et al. ............... 399/91 |
| 6,255,363 B1 | | 7/2001 | Baker et al. ................. 523/201 |
| 6,296,931 B1 | | 10/2001 | Azizi et al. ................. 428/340 |
| 6,391,954 B1 | | 5/2002 | Azizi et al. ................. 524/306 |
| 6,570,840 B1 | | 5/2003 | Wilkinson et al. ....... 369/257.4 |
| 6,668,104 B1 | | 12/2003 | Mueller-Fielder et al. .... 385/12 |

* cited by examiner

*Primary Examiner*—Layla Lauchman
*Assistant Examiner*—Tri Ton
(74) *Attorney, Agent, or Firm*—Mark A. Litman & Associates, P.A.

(57) ABSTRACT

A method and apparatus for evaluating the scattering properties of a transparency image comprises projecting radiation through the transparency image to form a transmitted beam of radiation; splitting the transmitted beam of radiation into at least two distinct beams of radiation, a first distinct beam and a second distinct beam; measuring a first amount of energy in the first distinct beam that corresponds to non-scattered light; measuring a second amount of energy in the second distinct beam that corresponds to scattered light; and comparing the first amount of energy to the second amount of energy to determine the proportion of the transmitted beam of radiation that is not scattered.

18 Claims, 3 Drawing Sheets

OVERHEAD TRANSPARENCY CLARITY SIMULATOR

BACKGROUND OF THE INVENTION

1. Field of the Invention

The present invention relates to the field of electrophotographic imaging and particularly to the field of electrophotographic imaging on transparent surfaces that are used to project images, as with overhead transparencies.

2. Background of the Art

Electrophotography forms the technical basis for various well-known imaging processes, including photocopying and some forms of laser printing. Other imaging processes use electrostatic or ionographic printing. Electrostatic printing is printing where a dielectric receptor or substrate is "written" upon imagewise by a charged stylus, leaving a latent electrostatic image on the surface of the dielectric recepetor. This dielectric receptor is not photosensitive and is generally not re-useable. Once the image pattern has been "written" onto the dielectric receptor in the form of an electrostatic charge pattern of positive or negative polarity, oppositely charged toner particles are applied to the dielectric receptor in order to develop the latent image. An exemplary electrostatic imaging process is described in U.S. Pat. No. 5,176,974.

In contrast, electrophotographic imaging processes typically involve the use of a reusable, light sensitive, temporary image receptor, known as a photoreceptor, in the process of producing an electrophotographic image on a final, permanent image receptor. A representative electrophotographic process involves a series of steps to produce an image on a receptor, including charging, exposure, development, transfer, fusing, and cleaning, and erasure.

In the charging step, a photoreceptor is covered with charge of a desired polarity, either negative or positive, typically with a corona or charging roller. In the exposure step, an optical system, typically a laser scanner or diode array, forms a latent image by selectively exposing the photoreceptor to electromagnetic radiation, thereby discharging the charged surface of the photoreceptor in an imagewise manner corresponding to the desired image to be formed on the final image receptor. The electromagnetic radiation, which may also be referred to as "light", may include infrared radiation, visible light, and ultraviolet radiation, for example.

In the development step, toner particles of the appropriate polarity are generally brought into contact with the latent image on the photoreceptor, typically using a developer electrically-biased to a potential of the same polarity as the toner polarity. The toner particles are more strongly attracted to the discharged regions of the photoreceptor and migrate to the photoreceptor and selectively adhere to the latent image via electrostatic forces, forming a toned image on the photoreceptor.

In the transfer step, the toned image is transferred from the photoreceptor to the desired final image receptor; an intermediate transfer element is sometimes used to effect transfer of the toned image from the photoreceptor with subsequent transfer of the toned image to a final image receptor. The transfer of an image typically occurs by one of the following two methods: elastomeric assist (also referred to herein as "adhesive transfer") or electrostatic assist (also referred to herein as "electrostatic transfer").

Elastomeric assist or adhesive transfer refers generally to a process in which the transfer of an image is primarily caused by balancing the relative energies between the ink, a photoreceptor surface and a temporary carrier surface or medium for the toner. The effectiveness of such elastomeric assist or adhesive transfer is controlled by several variables including surface energy, temperature, pressure, and toner rheology. An exemplary elastomeric assist/adhesive image transfer process is described in U.S. Pat. No. 5,916,718.

Two types of toner are in widespread, commercial use: liquid toner and dry toner. The term "dry" does not mean that the dry toner is totally free of any liquid constituents, but connotes that the toner particles do not contain any significant amount of solvent, e.g., typically less than 10 weight percent solvent (generally, dry toner is as dry as is reasonably practical in terms of solvent content), and are capable of carrying a triboelectric charge.

A typical liquid toner composition generally includes toner particles suspended or dispersed in a liquid carrier. The liquid carrier is typically nonconductive dispersant, to avoid discharging the latent electrostatic image. Liquid toner particles are generally solvated to some degree in the liquid carrier (or carrier liquid), typically in more than 50 weight percent of a low polarity, low dielectric constant, substantially nonaqueous carrier solvent. Liquid toner particles are generally chemically charged using polar groups that dissociate in the carrier solvent, but do not carry a triboelectric charge while solvated and/or dispersed in the liquid carrier. Liquid toner particles are also typically smaller than dry toner particles. Because of their small particle size, ranging from about 5 microns to sub-micron, liquid toners are capable of producing very high-resolution toned images. This distinguishes dry toner particles from liquid toner particles.

A typical toner particle for a liquid toner composition generally comprises a visual enhancement additive (for example, a colored pigment particle) and a polymeric binder. The polymeric binder fulfills functions both during and after the electrophotographic process. With respect to processability, the character of the binder impacts charging and charge stability, flow, and fusing characteristics of the toner particles. These characteristics are important to achieve good performance during development, transfer, and fusing. After an image is formed on the final receptor, the nature of the binder (e.g. glass transition temperature, melt viscosity, molecular weight) and the fusing conditions (e.g. temperature, pressure and fuser configuration) impact durability (e.g. blocking and erasure resistance), adhesion to the receptor, gloss, and the like.

Polymeric binder materials suitable for use in liquid toner particles typically exhibit glass transition temperatures of about −24° C. to 75° C., which is lower than the range of glass transition temperatures (50–100° C.) typical for polymeric binders used in dry toner particles. In particular, some liquid toners are known to incorporate polymeric binders exhibiting glass transition temperatures ($T_g$) below room temperature (25° C.) in order to rapidly self fix, e.g., by film formation, in the liquid electrophotographic imaging process; see e.g. U.S. Pat. No. 6,255,363. However, such liquid toners are also known to exhibit inferior image durability resulting from the low $T_g$ (e.g. poor blocking and erasure resistance) after fusing the toned image to a final image receptor.

In other printing processes using liquid toners, self-fixing is not required. In such a system, the image developed on the photoconductive surface is transferred to an intermediate transfer belt ("ITB") or intermediate transfer member ("ITM") or directly to a print medium without film formation at this stage. See, for example, U.S. Pat. Nos. 5,410,392 to Landa, issued on Apr. 25, 1995; and U.S. Pat. No.

5,115,277 to Camis, issued on May 19, 1992. In such a system, this transfer of discrete toner particles in image form is carried out using a combination of mechanical forces, electrostatic forces, and thermal energy. In the system particularly described in the '277 patent, DC bias voltage is connected to an inner sleeve member to develop electrostatic forces at the surface of the print medium for assisting in the efficient transfer of color images.

Since the introduction of electrophotographic copying and printing machines using dry toner powder particles to develop electrostatic images, there has been a continuing emphasis on toner image transfer with faithful, high quality, durable fused image reproduction on the surface of a receptor sheet. Previous studies related to the quality of images produced by transfer of toner powder, from imaging drums of electrophotographic copiers and printers to suitable recording sheets, focused attention on the bond formed between the powder and the recording sheet. Having demonstrated sufficient adhesion, measurement of optical density indicated the intensity of the image formed on the recording sheet, as shown by U.S. Pat. No. 5,451,458. U.S. Pat. No. 5,302,439 discloses a recording sheet which comprises a substrate and a coating thereon Materials from the various groups increase the adhesion of toner powder to the recording sheet.

More recently, attention has turned to improvement of the projected transparency of images formed by fusing dry toner particles to transparent receptor films, Poor transparency of fused dry toner images is believed to result from multiple light scattering from solid particles (e.g. pigment particles) having a volume mean diameter generally larger than approximately 0.5–1 micron, such that light projected through the fused toner layer undergoes multiple scattering from the solid particles. Alternatively, multiple light scattering may occur at the surfaces and edges of the fused transparency image when the projector's light source is transmitted through the fused toned image on the transparency receptor.

The problem of light scattering is particularly undesirable and tends to be more noticeable with the use of colored pigments. In the use of black and white images, light scatter tends to only cause increased opacity or increased transmission optical density of the projected image, which is minimally problematic, as the projected image actually appears more black. However, when light is scattered by multicolored pigment particles, there is a color shift effected, and this results in not only altering the transmitted optical density and projected image opacity, but also the color content itself. The imaging process must retain the ability to provide high fidelity to the intended colors and high color quality when the fused toned image on the receptor film is projected, or the image quality will be seriously degraded. For example, one of the most apparent scattering effects is noted in overhead projection of toned yellow colors, where the projected yellow image is often "muddy," appearing as gold, light green, brown or even black, depending upon smoothness of the fused toner film and the extent of light scattering from both the surface and the volume of the fused toned image.

Various approaches have been used in the art to improve the projected transparency of fused dry toner images. One approach involves alteration of the toner composition to improve uniformity of the fused toner layer on the transparent image receptor. U.S. Pat. No. 5,635,325 discloses a core/shell toner for developing electrostatic images including a binder resin, a colorant and an ester wax, wherein the core melts and acts as a release agent during fusing, eliminating the need for silicone based release agents to be applied to the fuser rolls.

Other approaches to improve the projection quality of fused dry toner images on transparency receptors involve use of special coatings on the transparency receptor to improve coalescence of the toner powders into a smooth, uniform layer on the receptor. U.S. Pat. Nos. 5,208,093, 4,298,309 and 5,635,325 disclose a variety of solutions to achieve miscibility of the coated film with the toner while maintaining low melt viscosity. U.S. Pat. No. 5,451,458 discloses a recording sheet which comprises a substrate and a coating thereon containing a binder selected from polyesters, polyvinyl acetals, vinyl alcohol-vinyl acetal copolymers, polycarbonates, and mixtures thereof, and an additive having a melting point of less than about 65 degree C. and a boiling point of more than about 150 degree C. U.S. Pat. Nos. 6,391,954 and 6,296,931 describe a recording sheet including an additive, referred to as a compatibilizer, to improve the quality of images formed by toner powder development of electrostatic charge patterns.

Still other approaches are directed at improved toner transparency using special fixing methods for fusing the dry toner powder to the receptor sheet. U.S. Pat. No. 5,824,442 describes the use of special toners in such a fixing method. U.S. Pat. No. 5,519,479 describes a fusing or fixing device for use in an electrophotographic apparatus, comprising a pair of pressing means opposing each other to form therebetween a nip through which an image supporting member supporting an unfixed toner image is passed so that the toner image is fixed to the image supporting member, wherein one of the pressing means which contacts the toner image on the image supporting member has a layer formed of a soft matrix and granular particles dispersed in the matrix and having greater hardness than the matrix, whereby fine irregularities are formed on toner surfaces on the image supporting member by the granular particles under application of pressure during fixing. This is clearly contraindicated as a solution against light scattering that shifts color balance and fidelity.

For the case of fused liquid toner images on transparent receptor sheets, all of the previously described problems may occur. Poor fused toner adhesion, unacceptable projected image transparency due to light scattering by over-sized pigment particles or surface irregularities in the fused toner layer, and poor color fidelity in multi-color fused toner images remain problematic. In addition, the difficulty of producing durable, transparent, multi-colored fused liquid toner images on transparency receptors is compounded by the fact that a substantial amount of carrier liquid is typically present in the toned image prior to fusing on the final transparency receptor. The latter issue is particularly problematic for transparencies produced using liquid electrophotographic imaging processes that make use of an electrostatic transfer assist to transfer the toned image to the final image receptor, because a substantial amount of carrier liquid is required in the toned image in order to effect electrostatic transfer. This carrier liquid may have adverse effects on the durability of the fused liquid toner image if it remains in the fused image. Alternatively, removal of the carrier liquid may have adverse effects on the transparency and color fidelity of the projected liquid toned image.

Copending U.S. patent application Ser. No. 10/750,458, filed Dec. 31, 2003, titled "REDUCED LIGHT SCATTERING IN PROJECTED IMAGES FORMED FROM ELECTROGRAPHIC TONERS" discloses a method for improving the light-scattering properties of electrographic toned images used in transparencies. That application is incorporated herein by reference. It is still necessary to identify, measure and otherwise evaluate the quality of projected transparency images to determine how and when the image or the projection facility must be modified or improved.

Optical systems have been used in many varied fields of technology for measuring conditions and properties. The optical systems can be extremely simple, measuring the required or unwanted presence of light or radiation (e.g., Ultraviolet light, visible light, or infrared radiation), or by more complex systems that determine and/or measure the properties of light at specific locations (including wavelengths, phases, intensity, patterns and the like). A grating spectrometer is an example of a complex optical staring] spectrum analyser. This works by splitting the input beam into many hundreds of beams, changing the phase of each beam by an amount which depends linearly on its position (using the grating) and recombining all of the phase shifted beams on an output detector array. Because of the phase shifts, different optical frequencies recombine in phase at different places in the detector array.

Another type of staring optical spectrum analyser is an acoustic-optic device in which the signal to be analysed is used to drive an acoustic-optic transducer which launches an acoustic wave into a transparent piezoelectric and electro-optic material (e.g. lithium niobate). The acoustic waves can set up refractive index waves in such materials which diffract a light beam passing through them by an amount directly proportional to the RF frequency. In practice, this type of spectrum analyser can give very high resolution, mainly because acoustic waves travel much more slowly than electromagnetic waves, allowing longer delays to be achieved in short devices. However, they tend to be limited to frequencies below a few GHz because of acoustic losses.

U.S. Pat. No. 5,132,627 (Popovic et al.) teaches a motionless scanner for use in electrophothgraphy. In its disclosure, a beam splitter is used in certain instances. It is disclosed that exposure light is transmitted through an electrode 16 to photoreceptor 10. For tests which require on-line monitoring of exposure light intensity a beam splitter 32 deflects a portion of the illumination light to a photodiode 33. Coulomb meter 29a is used in two ways, either to measure charge flow through the photoreceptor sample or to monitor the illumination light energy by measuring the charge flow through photodiode 33. Most instruments such as electrostatic meter 28, coulomb meter 29a, exposure light source 31 and high voltage supply 20 are connected directly to the data acquisition board of computer 30, but others such as relay 24 utilize simple interface circuitry.

U.S. Pat. No. 5,543,177 (Morrison et al.) teaches marking materials containing retroreflecting fillers describes the use of retroreflectors as timing marks on a photoreceptor belt used in xerographic copiers and printers was simulated as follows. In a typical prior art machine, the standard timing marks on belt photoreceptors are rectangular holes in the opaque ground strip. A light source is put on one side of the belt, a detector on the other. The time at which the timing hole passes can be determined by situating a light source on one side of the belts and a detector on the other. (Another method to detect the hole is to use an infrared source to illuminate the opaque ground strip as it moves.) The illuminating beam comes from a nanometer wavelength light emitting diode. By passing the beam through a beam splitter, the light reflected off the conductive ground plane can be detected at nearly 90 degree specular reflectance. Such a device is a Xerox® 1075 CIRD (part number 130S941, Xerox Corp., Rochester, N.Y.). If the illumination falls on the timing hole, no light is reflected.

U.S. Pat. No. 6,668,104 (Mueller-Fiedler et al.) describes a method for detecting the wetting of a surface, for example, a windshield on a vehicle, using optical sensing. A beam splitter is suggested as one format for providing the optical (including infrared) beam. Light from the visible range or the infrared range is coupled into the windshield from the inside of the windshield. The unmoistened outer surface reflects the light, which reaches a receiver. To increase the efficiency, the light is shone in in such a way that total reflection takes place on the outside. The total reflection is disturbed by the wetting of the outer surface with water. It is a common feature of all the known versions that the input and output of the electromagnetic waves take place at spatially markedly separate points, and that the sensor element and the evaluation electronics are accommodated in a common housing. Error-free signal detection can then be accomplished only if the optical sensor is mounted in a region of the windshield that is cleaned by the windshield wiper system. Therefore in some vehicle types, the sensor has to be mounted at a distance of up to 15 cm from the upper edge of the windshield. A disadvantage of this is that the sensor housing in these cases is within the field of view of the driver and is perceived as annoying because of the lack of transparency. Miniaturization is not possible, since for timely detection of wetting, for instance when it is beginning to rain, a sensor region approximately 4–5 $cm^2$ in area is necessary.

U.S. Pat. No. 6,570,840 (Wilkinson et al.) discloses improvements in the transverse sectional shape of three-dimensional features displayed in optical recording structures—discs, cylinders, cards, multi-layered devices and structures replicated from them—to increase Figure of Merit. The cross-sectional shape improvements include reductions in berm height and width, dual level data marks and tracking guides, and land areas projecting above or into the surface of the recording structure. Disclosed methods include dual and/or dithered beam writing onto the structure and improved composition of the active layer of the structure. Also disclosed are apparatus for producing such improved features on optical recording structures, according to one or more of the disclosed methods. In one embodiment, a dithered secondary beam whose intensity is greater, and whose focused spot size is narrower, than the secondary beam configuration previously described. In this embodiment, the secondary beam is dithered—oscillated rapidly in a radial direction, in respect to the disc—while trough formation occurs. A variation of the latter embodiment comprises use of beam splitting to produce a plurality of overlapping, side-by-side non-dithering beams whose sum is a beam of essentially uniform intensity along all or a portion of its width. A further variation comprises beam dithering without beam splitting, where the single beam executes a complex dithering motion that is radial in respect to the disc (i.e., transverse, in respect to the longitudinal dimension of the formed features), and thus may produce pits and a trough simultaneously.

U.S. Pat. No. 6,055,391 (Jackson et al.) describes a system for detecting and damping vibrations in printer components, mechanical devices, buildings, or large structures has a plurality of light beam detectors for generating signals corresponding to a reference light beam position. The light beam detectors are partially transparent to allow passage of the light beam through the detector, permitting multiple detectors to use the same reference light beam. The detectors are attached to vibration susceptible structural elements, with detected movement of the light beam with respect to the partially transparent light beam detector corresponding to movement of the vibration susceptible structural element. Motion control units connected to the detectors can be used to control or damp detected vibrations in real-time. The printer system may have a vibration detection and suppression unit mounted on the inside of a panel. The unit may include a laser light beam source that directs a light beam to pass through a number of partially transparent light beam detectors distributed along the panel. In one embodiment, a beam splitter and mirrors are used to redirect the light beam to those detectors not in direct line with the laser light beam source. Other light beam redirecting or bending systems can be used, including light scanners, polygon scanners, fiber optics, or prisms. For certain applications, design of detectors capable of refractive bending of light to redirect a beam pass through is contemplated (e.g. prism detectors). If information regarding light edge position, rather than light spot position is adequate (e.g. in conjunction with one dimensional detectors), various light diffusers or spreaders can also be used.

U.S. Pat. No. 5,790,255 describes a system of partially transparent light beam detectors that allow passage of the light beam through the detector allows multiple detectors that use the same reference light beam. Transparent detectors can be position sensitive detectors (PSD), photodiode arrays, or CCD imaging arrays. The detectors are attached to vibration susceptible structural elements, with detected movement of the light beam with respect to the partially transparent light beam detectors corresponding to movement of the vibration susceptible structural element.

It is desirable in the improvement of transparency images to have a system that can actually determine the quality of the image under projection conditions without having to project the image on a screen and make a qualitative or visual interpretation of the quality.

SUMMARY OF THE INVENTION

A system and apparatus are provided to quantitatively or qualitatively measure scatter from radiation or light projection through a transparency. After coherent radiation (e.g., laser radiation) passes through the transparency, at least two distinct beams are split from the transmitted radiation. One of the at least two split beams measures transmitted radiation (within a particular angular distribution) and at least one other of the at least two split beams measures scattered radiation (outside a particular angular distribution). A ratio of the two measurements provides a highly accurate measure of the light scattering effect of the transparency, which is a major cause of poor color fidelity in transparencies.

DETAILED DESCRIPTION OF THE INVENTION

The projection of transparency material has been a popular medium for augmentation of visual presentations. Many different imaging formats are able to provide transparencies from digital or analog data. Ink jet printers are popular engines for generating transparencies. As previously noted, however, transparency images, including those from ink jet printers, can suffer from image quality defects resulting from light scattering. The present system and apparatus can be used to qualitatively or quantitatively determine the existence of intolerable or undesirable levels of scatter that affect color resolution. Present analysis of image quality has been essentially limited to subjective observation by actually projecting the image on a screen and determining whether or not the image is good or bad. This is highly inefficient and subjective.

The inventive device and system provides a simulation of projected optical scattering through a transparency, preferably using one or more monochromatic illumination beams (preferably collimated or at least focused beams) that pass through an image (preferably a single color toned/inked/printed image). The use of a monochromatic source assists in removing or reducing the visual subjectivity of color perception from an evaluation process. This makes subsequent optimization of transparency quality more objective and provides a standard or consistent basis for evaluating and comparing transparency quality.

As is known to color scientists, many individual colors are actually composites of different wavelengths. When scattering of visible light occurs, the scattering is at least in-part dependent upon the wavelength of the components of the color, the physical features causing scattering (e.g., particle size, surface are, edge shape, etc.), and other physical factors. It has therefore been difficult to predict and compare scatter effects, except through subjective evaluation.

Reference to the Figures will assist in better understanding of the present invention.

Figure 1:
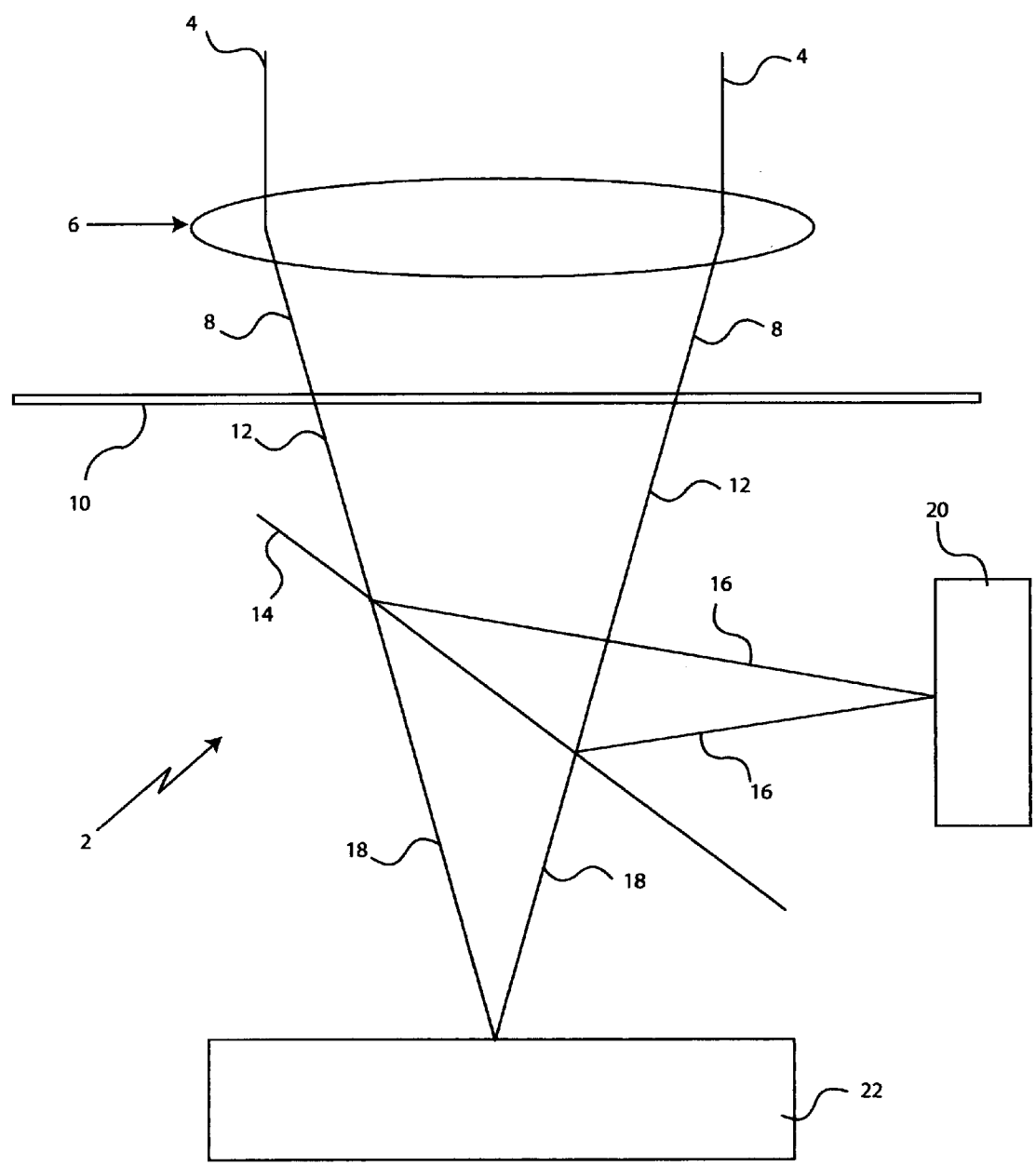
FIG. 1 shows a schematic of a Transparency Projection Simulator according to an aspect of the invention.

FIG. 1 shows a schematic of a Transparency Projection Simulator system 2 according to an aspect of the invention. The system 2 comprises a source of radiation (e.g., visible laser light, infrared radiation, or ultraviolet light) 4, a focusing lens 6, producing focused light 8. The focused light 8 passes through a transparency 10 (usually on a support or supported at its ends, not shown) to produce a stream of light 12 that has been affected by passage through the transparency 10. The stream of light 12 then is modified by a beam splitter 14 (as conventionally known in the art) to provide two distinct beams of light 16, 18. One of the distinct light beams (e.g., 16 ) is directed to a first transmitted light detector 20 and a second of the distinct light beams 18 is directed towards a second scattered light detector 22. The beam splitter may apportion the stream of light 12 into any proportion of light that is useful for measurement of the amount of light impacting each detector 20, 22. The light, for example may be apportioned equally (50% as beam 16 and 50% as beam 18 ) or in proportions from, for example, from 5–95% as transmitted beam 16 and 95–5% as scattered beam 18. A preferred range of apportionment is between 25–75% transmitted beam and 75–25% scattered beam, respectively.

The terminology of "transmitted beam" and "scattered beam" is not meant to imply that all light in each beam is either scattered or transmitted (without deviation), but rather that the beam will be used primarily to measure uniformly transmitted light and scattered light.

Figure 2:
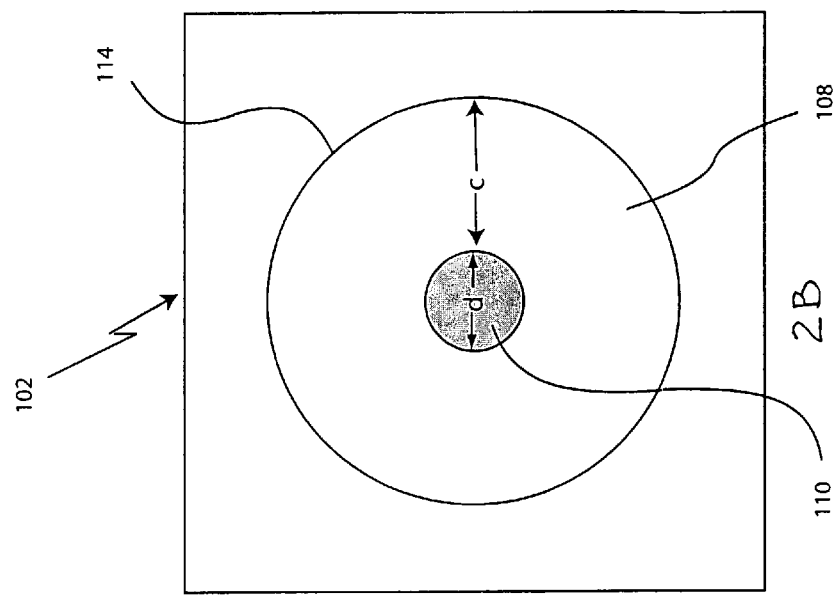
FIG. 2 shows side-by-side projections onto a detector surface for transmitted and scattered radiation.
Figure 2:
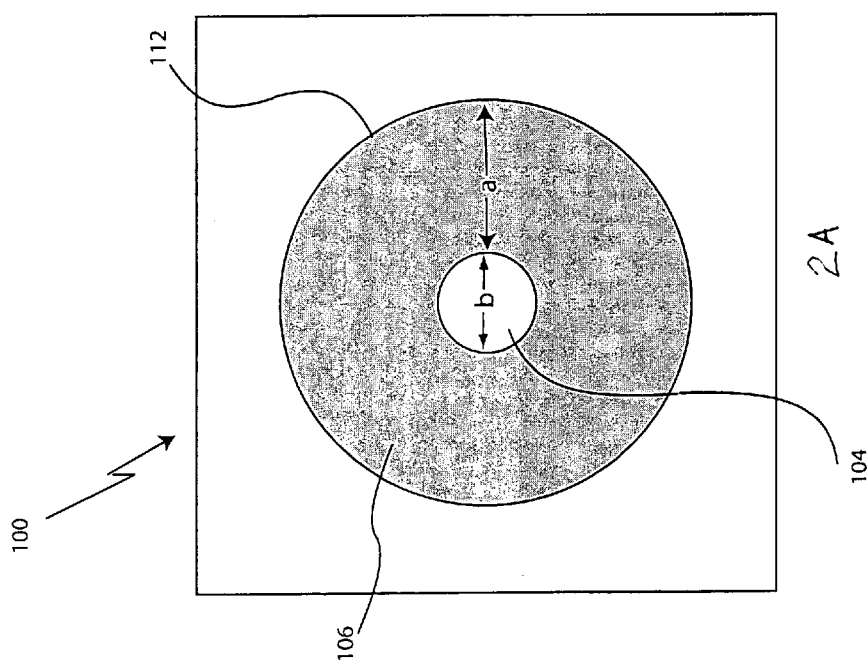

FIG. 2 shows two side-by-side detectors 100 and 102, for receiving and detecting transmitted light and scattered light, respectively. Detector 100 has a central area 104 of the detector 100 with a diameter b that will detect and preferably measure light energy within that area 104. That area 104 is surrounded by a masked, light opaque, or otherwise energy-absorbing or energy-measuring neutralized area 106 where scattered light associated with the transmitted energy beam would strike the transmitted light detecting plate 100. The linear distance a is the distance along a diameter of the circular spot shape 112 that is opacified. The expected shape of the cross-section of the beam is represented by area 112. Detector 102 for measuring scattered light is essentially the inverse of detector 100. The approximate shape of the spot area 114 is shown as central opaque area 110 with diameter d (preferably approximately equal to diameter b of detector 100, as is linear distance c representing the distance along a diameter of the circular spot shape 114 that is energy-detecting) and energy-absorbing area 108. Each of the energy-absorbing areas measures the total amount of light energy striking that area at any particular time, and data on that that energy is transmitted to a processor or information storage device.

The data on the measured energy in each of the respective areas can be used in a number of ways to determine a quantitative value for scatter. For purposes of explanation, it will be assumed that the beam splitter apportions the original transmitted beam (12 from FIG. 1) 30% to the transmitted light detector and 70% to the scattered light detector. For example, the energy striking area 104 in the transmitted light detector 100 should be 100% of the beam splitter redirected transmitted light (e.g., that has passed through the transparency. Although the energy of the original beam is known, unless the transmission characteristics of the transparency and the beam are precisely matched (that is, the transparency transmits 100% of the wavelength of the 30% of the beam apportioned to the transmitted light beam), there will always be some loss of energy from the original beam by spectral absorption. Therefore, a measurement with only one of the detector areas (104 or 108) would be less precise, without consideration and calculation or estimation of the amount of energy from the original beam from spectral absorption in the transparency.

The detected and measured amount of energy in each of the areas 104 (for the transmitted light ($\lambda_T$) and 108 (for the scattered light $\lambda_S$) are evaluated as a ratio of either $$(\lambda_T)/\lambda_S) \text{ or } (\lambda_S)/(\lambda_T)$$

and these ratio values considered to determine the quality of the transparency image based on light scattering effects. As a thumbnail estimate, it is often found that a ratio of $(\lambda_S)/(\lambda_T) \leq 3.0$ is most desirable, and conversely a ratio of $(\lambda_T)/(\lambda_S) \geq 0.334$ is also desirable.

Because each detector is placed in the focus plane (or Fourier plane) of the focusing lens 6, the masks are usually provided as Fourier transform filters that operate on the incoming light (the specular light referred to as the transmitted light) and block the scattered light, or conversely in the scattered light detector block most of the specular light and pass most of the scattered light.

The system essentially models the light scattered from a transparency sample as if it were diffracted light and then operates in the Fourier Transform plane of the focusing lens, which is the analog of the fresnel light directing lens in a transparency projector (the one just below the transparency platen) such as the 3M Model 9200 imaging lens. The incident light consists of only specular light until it interacts with the transparency, at which time some of the specular light passes through without modification and some is converted to components of other spatial frequencies which scatter off the main direction of the light beam and miss the imaging lens in the projector. Thus, the detectors in the simulator are the analog of the entrance pupil of the imaging lens in the projector. This scattered light can be generated by particles in the ink layer, by voids in the ink layer or by a rough surface on the ink layer being projected on the transparency projector.

Figure 3:
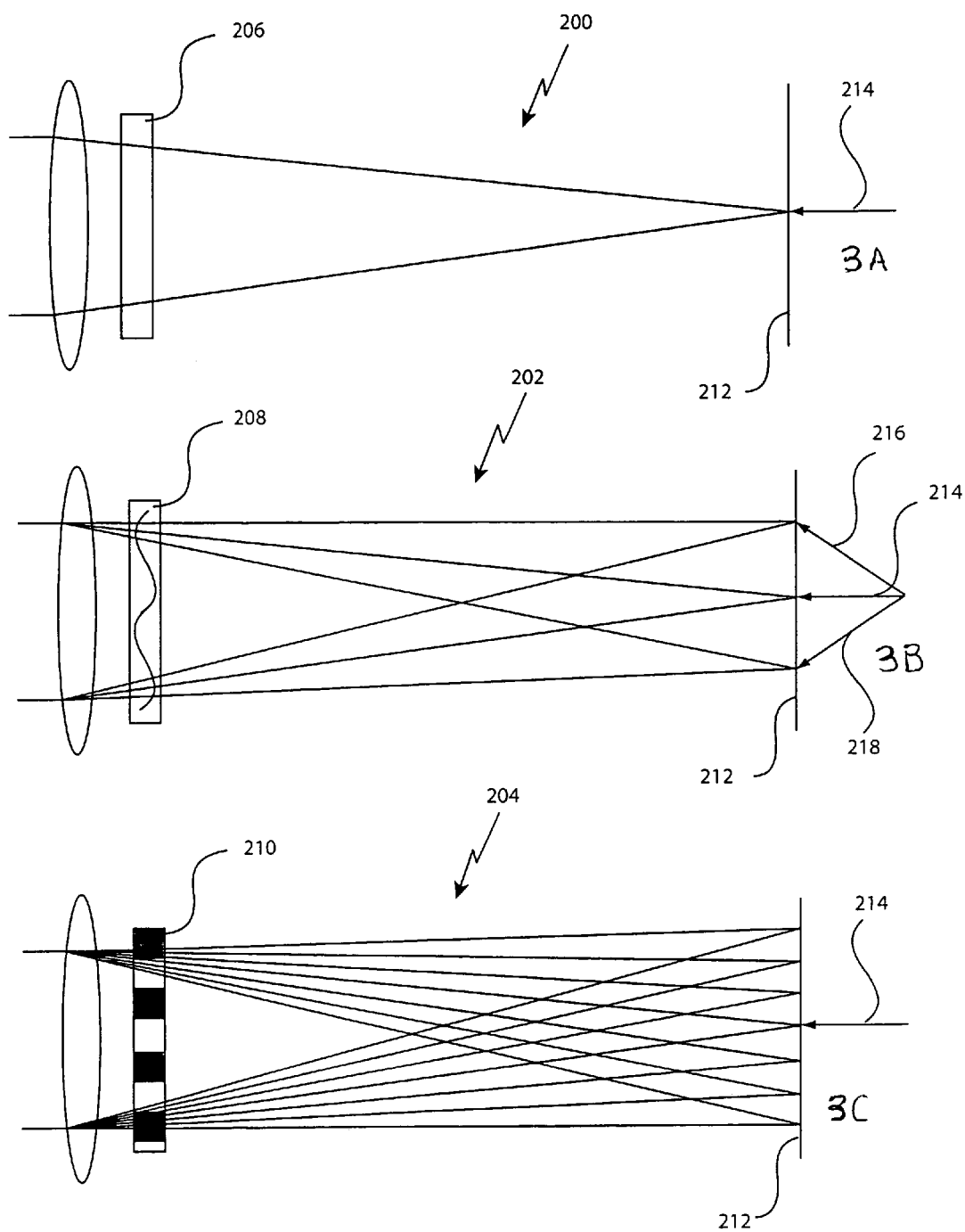
FIGS. 3a, 3b and 3c show a schematic of clear sample projection through a transparency, sinusoidal intensity variation with frequency (F) through a transparency, and square wave intensity variation with frequency (F) through a transparency, respectively.

FIGS. 3a, 3b and 3c show schematic representations of clear sample projection through a transparency 200, sinusoidal intensity variation with frequency (F) through a transparency 202, and square wave intensity variation with frequency (F) through a transparency 204, respectively. In the clear sample 200 schematic, the clear sample 206 produces a single light spike 214 on the focal plane 212 at the optical axis. This is the specular component or the non-scattered component. In the second schematic 202 showing sinusoidal intensity variation with frequency (F), the scattering transparency 208 produces three light spikes 214 (the specular component on the optical axis), 216 and 218 on the focal plane 212. In the third schematic 204 showing square wave intensity variation with frequency (F), the scattering transparency 210 produces multiple light spikes (seven shown), including 214 (the specular component on the optical axis) on the focal plane 212.

A perfect (non-scattering) transparency would act like the schematic shown in 200, where all light passes through the transparency and no light is scattered by the ink layer. The schematic 202 represents a case where only a small amount of light is scattered (deflected away from the optical axis) by the ink layer, and it is only that small amount of light that may not enter the imaging lens on a transparency projection system (depending in part upon the size and distance of the transparency lens). The ratio of scattered radiation (216 plus 218) to the specular radiation (214) is below 3:1, and the image retains an acceptable level of color fidelity. The third schematic 204 represents a significant amount of optical noise caused by scattering of the beam by imperfections in the ink image on the transparency. The optical noise is caused by significant haze or non-uniformities and defects in the ink image which strongly scatters radiation in the incident beam. This causes significant radiation (e.g., all of the radiation other than the specular radiation 214) to not be received by the imaging lens of the transparency projector. The missing light (the light that misses the imaging lens) causes a shift in perceived color and intensity of the projected light. In the case of projected yellow, the projected color appears darker, and the color tone is shifted towards a more gold color. If the scatter is significantly great, the projected 'yellow' may even appear black.

In the invention, light is made to be incident onto a transparency sample and the transmitted beam is rendered into two beams by a beam-splitter (a piece of glass with a light coating of aluminum so that X% transmits and Y% reflects). In the case of this invention, a 70/30 (transmitted/reflected) splitter is used but 50/50 or other ratios would work.

The reflected beam is made to focus to a spot and in the plane of best focus; an aperture-limited detector is positioned. This channel contains the transmission detector which passes the DC (specular) component and blocks the scattered component. The transmitted beam is made to focus on the scattered light detector which blocks the DC and passes the scattered light.

Because the illumination in this device is a monochromatic laser beam (LED source could also work and even white light could work as illumination) the color of ink used to make a given transparency greatly changes the amount of laser light that passes through a test area on the sample transparency. If the laser beam is red in color, for example, then even a very good cyan transparency will absorb much more light than a good yellow transparency. This is why the output values of the two detectors are used in ratio to each other.

The output of this device may be calculated as follows:

[Scattered Light Intensity]/[Transmitted Light Intensity]=SCORE

As with most relative value ratios, the units of measurement are insignificant, as long as the units are the same as between the Scattered Light Intensity and the Transmitted Light Intensity. By experimentation, if SCORE<3.0, Transparency is excellent. By the same token, if SCORE>10, Transparency is bad. If 10>SCORE>3, then the transparency is marginal and could be improved but it isn't really unacceptable in all presentation formats (yellow may be slightly gold and cyan and magenta could be a little "muddy").

EXAMPLES

In order to demonstrate the scope and practice of the present invention, a variety of liquid toners were electrophotographically printed onto transparent sheets suitable for use in overhead projection (OHP). The preparation details for the following liquid toner compositions and details of the liquid toner electrophotographic printing method are generally disclosed in Copending U.S. patent application Ser. No. 10/612,533, filed Jun. 30, 2003, entitled "ORGANOSOL INCLUDING AMPHIPATHIC COPOLYMERIC BINDER MADE WITH SOLUBLE HIGH $T_G$ MONOMER AND LIQUID TONERS FOR ELECTROPHOTOGRAPHIC APPLICATIONS," claiming priority to U.S. Provisional Application Ser. No. 60/425,467, filed Nov. 12, 2002, entitled "ORGANOSOL INCLUDING AMPHIPATHIC COPOLYMERIC BINDER MADE WITH SOLUBLE HIGH $T_G$ MONOMER AND LIQUID TONERS FOR ELECTROPHOTOGRAPHIC APPLICATIONS," which applications are incorporated herein by reference in their entirety.

Liquid Toner Composition Test Methods and Apparatus

In the following liquid toner composition examples, percent solids of the graft stabilizer solutions and the organosol and ink dispersions were determined thermo-gravimetrically by drying in an aluminum weighing pan an originally-weighed sample at 160° C. for four hours, weighing the dried sample, and calculating the percentage ratio of the dried sample weight to the original sample weight, after accounting for the weight of the aluminum weighing pan. Approximately two grams of sample were used in each determination of percent solids using this thermo-gravimetric method.

In the practice of the invention, molecular weight is normally expressed in terms of the weight average molecular weight, while molecular weight polydispersity is given by the ratio of the weight average molecular weight to the number average molecular weight. Molecular weight parameters were determined with gel permeation chromatography (GPC) using tetrahydrofuran as the carrier solvent. Absolute weight average molecular weight were determined using a Dawn DSP-F light scattering detector (Wyatt Technology Corp., Santa Barbara, Calif.), while polydispersity was evaluated by ratioing the measured weight average molecular weight to a value of number average molecular weight determined with an Optilab 903 differential refractometer detector (Wyatt Technology Corp., Santa Barbara, Calif.).

Organosol and toner particle size distributions were determined by the Laser Diffraction Laser Diffraction Light Scattering Method using a Horiba LA-920 laser diffraction particle size analyzer (Horiba Instruments, Inc., Irvine, Calif.). Samples were diluted approximately 1/10 by volume in Norpar™ 12 and sonicated for one minute at 150 watts and 20 kHz prior to measurement in the particle size analyzer according to the manufacturer's instructions. Particle size was expressed as both a number mean diameter ($D_n$) and a volume mean diameter ($D_v$) and in order to provide an indication of both the fundamental (primary) particle size and the presence of aggregates or agglomerates.

The liquid toner conductivity (bulk conductivity, $k_b$) was determined at approximately 18 Hz using a Scientifica Model 627 conductivity meter (Scientifica Instruments, Inc., Princeton, N.J.). In addition, the free (liquid dispersant) phase conductivity ($k_f$) in the absence of toner particles was also determined. Toner particles were removed from the liquid medium by centrifugation at 5° C. for 1–2 hours at 6,000 rpm (6,110 relative centrifugal force) in a Jouan MR1822 centrifuge (Winchester, Va.). The supernatant liquid was then carefully decanted, and the conductivity of this liquid was measured using a Scientifica Model 627 conductance meter. The percentage of free phase conductivity relative to the bulk toner conductivity was then determined as 100% ($k_f/k_b$).

Toner particle mobility (dynamic mobility) was measured using a Matec MBS-8000 Electrokinetic Sonic Amplitude Analyzer (Matec Applied Sciences, Inc., Hopkinton, Mass.). Unlike electrokinetic measurements based upon microelectrophoresis, the MBS-8000 instrument has the advantage of requiring no dilution of the toner sample in order to obtain the mobility value. Thus, it was possible to measure toner particle dynamic mobility at solids concentrations actually preferred in printing. The MBS-8000 measures the response of charged particles to high frequency (1.2 MHz) alternating (AC) electric fields. In a high frequency AC electric field, the relative motion between charged toner particles and the surrounding dispersion medium (including counter-ions) generates an ultrasonic wave at the same frequency of the applied electric field. The amplitude of this ultrasonic wave at 1.2 MHz can be measured using a piezoelectric quartz transducer; this electrokinetic sonic amplitude (ESA) is directly proportional to the low field AC electrophoretic mobility of the particles. The particle zeta potential can then be computed by the instrument from the measured dynamic mobility and the known toner particle size, liquid dispersant viscosity, and liquid dielectric constant.

The charge per mass measurement (Q/M) was measured using an apparatus that consists of a conductive metal plate, a glass plate coated with Indium Tin Oxide (ITO), a high voltage power supply, an electrometer, and a personal computer (PC) for data acquisition. A 1% solution of ink was placed between the conductive plate and the ITO coated glass plate. An electrical potential of known polarity and magnitude was applied between the ITO coated glass plate and the metal plate, generating a current flow between the plates and through wires connected to the high voltage power supply. The electrical current was measured 100 times a second for 20 seconds and recorded using the PC. The applied potential causes the charged toner particles to migrate towards the plate (electrode) having opposite polarity to that of the charged toner particles. By controlling the polarity of the voltage applied to the ITO coated glass plate, the toner particles may be made to migrate to that plate.

The ITO coated glass plate was removed from the apparatus and placed in an oven for approximately 30 minutes at 50° C. to dry the plated ink completely. After drying, the ITO coated glass plate containing the dried ink film was weighed. The ink was then removed from the ITO coated glass plate using a cloth wipe impregnated with Norpar™ 12, and the clean ITO glass plate was weighed again. The difference in mass between the dry ink coated glass plate and the clean glass plate is taken as the mass of ink particles (m) deposited during the 20 second plating time. The electrical current values were used to obtain the total charge carried by the toner particles (Q) over the 20 seconds of plating time by integrating the area under a plot of current vs. time using a curve-fitting program (e.g. TableCurve 2D from Systat Software Inc.). The charge per mass (Q/m) was then determined by dividing the total charge carried by the toner particles by the dry plated ink mass.

Liquid Toner Composition Materials

The following abbreviations are used in the compositions and examples:

EA: Ethyl acrylate (available from Aldrich Chemical Co., Milwaukee, Wis.)

EMA: Ethyl methacrylate (available from Aldrich Chemical Co., Milwaukee, Wis.)

DBTDL: Dibutyl tin dilaurate (a catalyst available from Aldrich Chemical Co., Milwaukee, Wis.)

HEMA: 2-Hydroxyethyl methacrylate (available from Aldrich Chemical Co., Milwaukee, Wis.)

TMI: Dimethyl-m-isopropenyl benzyl isocyanate (available from CYTEC Industries, West Patterson, N.J.)

TCHMA: Trimethyl cyclohexyl methacrylate (available from Ciba Specialty Chemical Co., Suffolk, Va.)

V-601: Dimethyl 2,2'-azobisisobutyrate (an initiator available as V-601 from WAKO Chemicals U.S.A., Richmond, Va.)

Liquid Toner Composition Nomenclature

Various liquid toner compositions were prepared for use in liquid electrophotographic printing of images on transparent final image receptors suitable for use in overhead projection (OHP). All of the liquid toners comprise a copolymeric binder dispersed in a carrier liquid, a pigment, and a charge director to promote chemical charging of the toner particles. The copolymeric binder dispersion in the carrier liquid is known in the art as an organosol. The organosol typically is made from amphipathic copolymeric particles comprising a carrier-soluble portion (designated the S portion or "shell") chemically bonded to a dispersed carrier-insoluble portion (designated the D portion or "core"). Chemical bonding of the S portion to the D portion is effected by incorporating a grafting site into the S portion to form a graft stabilizer precursor to the amphipathic copolymer. The graft stabilizer (S portion with grafting site) is chemically bonded to the D portion through the grafting site. The graft stabilizer acts to sterically stabilize the D portion with respect to aggregation.

In the following organosol and liquid toner compositions, the compositional details of each copolymer will be summarized by ratioing the weight percentages of monomers used to create the copolymer. The grafting site composition is expressed as a weight percentage of the monomers comprising the copolymer or copolymer precursor, as the case may be. For example, a graft stabilizer (precursor to the S portion of the copolymer) is designated TCHMA/HEMA-TMI (97/3-4.7) is made by copolymerizing, on a relative basis, 97 parts by weight TCHMA and 3 parts by weight HEMA, and this hydroxy functional polymer was reacted with 4.7 parts by weight of TMI.

Liquid Toner Composition 1

Graft Stabilizer Preparation

A 50 gallon reactor, equipped with a condenser, a thermocouple connected to a digital temperature controller, a nitrogen inlet tube connected to a source of dry nitrogen and a mixer, was thoroughly cleaned with a heptane reflux and then thoroughly dried at 100° C. under vacuum. A nitrogen blanket was applied and the reactor was allowed to cool to ambient temperature. The reactor was charged with 193 lb of Norpar™ 12, by vacuum. The vacuum was then broken and a flow of 1 CFM of nitrogen applied and the agitation is started at 70 RPM. 66.4 lb of TCHMA was added and the container rinsed with 2.6 lbs of Norpar™ 12. 2.10 lb of 98% HEMA was added and the container rinsed with 1.37 lbs of Norpar™ 12. Finally 1.03 lb of V-601 was added and the container rinsed with 0.2 lbs of Norpar™ 12. A full vacuum was then applied for 10 minutes, and then broken by a nitrogen blanket. A second vacuum was pulled for 10 minutes, and then agitation stopped to verify that no bubbles were coming out of the solution. The vacuum was then broken with a nitrogen blanket and a light flow of nitrogen of 1 CFH (cubic foot per hour) was applied. Agitation was resumed at 75 RPM and the mixture was heated to 75° C. and held for 16 hours. The conversion was quantitative.

The mixture was heated to 90° C. and held at that temperature for 1 hour to destroy any residual V-601, and then was cooled back to 70° C. The nitrogen inlet tube was then removed, and 1.06 lb of 95% DBTDL was added to the mixture using 1.37 lbs of Norpar™ 12 to rinse container, followed by 3.23 lb of TMI. The TMI was added drop wise over the course of approximately 5 minutes while stirring the reaction mixture and the container was rinsed with 1.4 lbs of Norpar™ 12. The mixture was allowed to react at 70° C. for 6 hours, at which time the conversion was quantitative.

The mixture was then cooled to room temperature. The cooled mixture was a viscous, transparent liquid containing no visible insoluble matter. The percent solids of the liquid mixture was determined to be 26.20% using thermo-gravimetric method described above. Subsequent determination of molecular weight was made using the GPC method described above; the copolymer had a $M_w$ of 276,950 and $M_w/M_n$ of 3.15 based on two independent measurements. The product is a copolymer of TCHMA and HEMA containing random side chains of TMI and is designed herein as TCHMA/HEMA-TMI (97/3-4.7% w/w) and can be used to make an organosol.

Organosol Preparation

A 560 gallon reactor, equipped with a condenser, a thermocouple connected to a digital temperature controller, a nitrogen inlet tube connected to a source of dry nitrogen and a mixer, was thoroughly cleaned with a heptane reflux and then thoroughly dried at 100° C. under vacuum. A nitrogen blanket was applied and the reactor was allowed to cool to ambient temperature. The reactor was charged with a mixture of 1522 lb of Norpar™ 12 and 99.9 lb of the graft stabilizer mixture from Example 1.1 @ 26.2% polymer solids along with an additional 9.5 lb of Norpar™ 12 to rinse the pump. Agitation was then turned on at a rate of 60 RPM, and temperature was check to ensure maintenance at ambient. Next 177 lb of EMA was added along with 28.5 lb Norpar$^{SM}$ 12 for rinsing the pump. 26.4 lb of EA was added with an additional 28 lb of Norpar™ 12 to rinse the pump. Finally 2.05 lb of V-601 was added, along with 9.5 lb of Norpar™ 12 to rinse the container. A full vacuum was then applied for 10 minutes, and then broken by a nitrogen blanket. A second vacuum was pulled for 10 minutes, and then agitation stopped to verify that no bubbles were coming out of the solution. The vacuum was then broken with a nitrogen blanket and a light flow of nitrogen of 0.5 CFH (cubic foot per hour) was applied. Agitation of 75 RPM was resumed and the temperature of the reactor was heated to 70° C. and maintained for 16 hours. The conversion was quantitative.

Next, 190 lb of n-heptane and 380 lb of Norpar™ 12 were added to the cooled organosol. The resulting mixture was stripped of residual monomer using a rotary evaporator equipped with a dry ice/acetone condenser. Agitation was held at 80 RPM and the batch heated to 95° C. The nitrogen flow was stopped and a vacuum of 126 torr was pulled and held for 10 minutes. The vacuum was then increased to 80, 50, and 31 torr, being held at each level for 10 minutes. Finally, the vacuum was increased to 20 torr and held for 30 minutes. At that point a full vacuum is pulled and 633 lbs of distillate was collected. The vacuum was then broken, and the stripped organosol was cooled to room temperature, yielding an opaque white dispersion. This organosol is designated TCHMA/HEMA-TMI//EMA/EA (97/3-4.7//87/13% w/w). The percent solid of the organosol dispersion after stripping was determined as 13.00% using thermogravimetric method described above. Subsequent determination of average particles size was made using the light scattering method described above; the organosol had a volume average diameter of 54.4 μm. The glass transition temperature was measured using DSC, as described above. The organosol had a $T_g$ of 60.97° C.

Liquid Toner Preparation 13846 g of organosol (from Example 1.2) @ 13.00% (w/w) solids in Norpar™ 12 was combined with 827 g of Norpar™ 12, 300 g Pigment Blue15:4 (PB:15:4, 249–3450, Sun Chemical Company, Cincinnati, Ohio and 27.12 g of 27.65% Zirconium HEX-CEM solution (OMG Chemical Company, Cleveland, Ohio). This mixture was then milled in a Hockmeyer HSD mill (Model HM1, Hockmeyer Equipment Corp. Elizabeth City, N.C.) charged with 4175 g of 0.8 mm diameter Yttrium Stabilized Ceramic Media. The mill was operated at 1500 RPM for 7.67 hours with water circulating through the jacket of the milling chamber at 45° C.

A 14% (w/w) solids toner concentrate exhibited the following properties as determined using the test methods described above:

Volume Mean Particle Size: 2.79 micron
Q/M: 293 μC/g
Bulk Conductivity: 267 picoMhos/cm
Percent Free Phase Conductivity: 0.86%
Dynamic Mobility: 7.50E–11 (m²/Vsec)

Liquid Toner Composition 2

Graft Stabilizer Preparation

A 50 gallon reactor, equipped with a condenser, a thermocouple connected to a digital temperature controller, a nitrogen inlet tube connected to a source of dry nitrogen and a mixer, was thoroughly cleaned with a heptane reflux and then thoroughly dried at 100° C. under vacuum. A nitrogen blanket was applied and the reactor was allowed to cool to ambient temperature. The reactor was charged with 193 lb of Norpar™ 12, by vacuum. The vacuum was then broken and a flow of 1 CFM of nitrogen applied and the agitation is started at 70 RPM. 66.4 lb of TCHMA was added and the container rinsed with 2.6 lbs of Norpar™ 12. 2.10 lb of 98% HEMA was added and the container rinsed with 1.37 lbs of Norpar™ 12. Finally 1.03 lb of V-601 was added and the container rinsed with 0.2 lbs of Norpar™ 12. A full vacuum was then applied for 10 minutes, and then broken by a nitrogen blanket. A second vacuum was pulled for 10 minutes, and then agitation stopped to verify that no bubbles were coming out of the solution. The vacuum was then broken with a nitrogen blanket and a light flow of nitrogen of 1 CFH (cubic foot per hour) was applied. Agitation was resumed at 75 RPM and the mixture was heated to 75° C. and held for 16 hours. The conversion was quantitative.

The mixture was heated to 90° C. and held at that temperature for 1 hour to destroy any residual V-601, and then was cooled back to 70° C. The nitrogen inlet tube was then removed, and 1.06 lb of 95% DBTDL was added to the mixture using 1.37 lbs of Norpar™ 12 to rinse container, followed by 3.23 lb of TMI. The TMI was added drop wise over the course of approximately 5 minutes while stirring the reaction mixture and the container was rinsed with 1.4 lbs of Norpar™ 12. The mixture was allowed to react at 70° C. for 6 hours, at which time the conversion was quantitative.

The mixture was then cooled to room temperature. The cooled mixture was a viscous, transparent liquid containing no visible insoluble matter. The percent solids of the liquid mixture was determined to be 26.20% using thermo-gravimetric method described above. Subsequent determination of molecular weight was made using the GPC method described above; the copolymer had a $M_w$ of 276,950 and $M_w/M_n$ of 3.15 based on two independent measurements. The product is a copolymer of TCHMA and HEMA containing random side chains of TMI and is designed herein as TCHMA/HEMA-TMI (97/3-4.7% w/w) and can be used to make an organosol.

Organosol Preparation

A 560 gallon reactor, equipped with a condenser, a thermocouple connected to a digital temperature controller, a nitrogen inlet tube connected to a source of dry nitrogen and a mixer, was thoroughly cleaned with a heptane reflux and then thoroughly dried at 100° C. under vacuum. A nitrogen blanket was applied and the reactor was allowed to cool to ambient temperature. The reactor was charged with a mixture of 1522 lb of Norpar™ 12 and 99.9 lb of the graft stabilizer mixture from Example 1.1 @ 26.2% polymer solids along with an additional 9.5 lb of Norpar™ 12 to rinse the pump. Agitation was then turned on at a rate of 60 RPM, and temperature was check to ensure maintenance at ambient. Next 177 lb of EMA was added along with 28.5 lb Norpar™ 12 for rinsing the pump. 26.4 lb of EA was added with an additional 28 lb of Norpar™ 12 to rinse the pump. Finally 2.05 lb of V-601 was added, along with 9.5 lb of Norpar™ 12 to rinse the container. A full vacuum was then applied for 10 minutes, and then broken by a nitrogen blanket. A second vacuum was pulled for 10 minutes, and then agitation stopped to verify that no bubbles were coming out of the solution. The vacuum was then broken with a nitrogen blanket and a light flow of nitrogen of 0.5 CFH (cubic foot per hour) was applied. Agitation of 75 RPM was resumed and the temperature of the reactor was heated to 70° C. and maintained for 16 hours. The conversion was quantitative.

190 lb of n-heptane and 380 lb of Norpar™ 12 were added to the cooled organosol. The resulting mixture was stripped of residual monomer using a rotary evaporator equipped with a dry ice/acetone condenser. Agitation was held at 80 RPM and the batch heated to 95° C. The nitrogen flow was stopped and a vacuum of 126 torr was pulled and held for 10 minutes. The vacuum was then increased to 80, 50, and 31 torr, being held at each level for 10 minutes. Finally, the vacuum was increased to 20 torr and held for 30 minutes. At that point a full vacuum is pulled and 633 lbs of distillate was collected. The vacuum was then broken, and the stripped organosol was cooled to room temperature, yielding an opaque white dispersion.

This organosol is designed TCHMA/HEMA-TMI//EMA/EA (97/3-4.7//87/13% w/w). The percent solid of the organosol dispersion after stripping was determined as 13.00% using thermo-gravimetric method described above. Subsequent determination of average particles size was made using the light scattering method described above; the organosol had a volume average diameter of 54.4 μm. The glass transition temperature was measured using DSC, as described above. The organosol particles had a $T_g$ of 60.97° C.

Liquid Toner Preparation

This is an example of preparing a magenta liquid toner at a weight ratio of organosol copolymer to pigment (O/P ratio) of 5 using the organosol prepared in example 1.2., for which the weight ratio of D material to S material was 8. 231 g of the organosol at 13.00% (w/w) solids in Norpar™ 12 were combined with 61 g of Norpar™ 12, 3.6

Pigment FR4580 (D.I.C), 1.8 g of Pigment RA1087 (Magruder Color Co., Elizabeth, N.J.) 0.6 g of RH0205 (Magruder Color Co., Elizabeth, N.J.), and 1.96 g of 6.11% Zirconium HEX-CEM solution (OMG Chemical Company, Cleveland, Ohio) in an 8 ounce glass jar. This mixture was then milled in a 0.5 liter vertical bead mill (Model 6TSG-1/4, Amex Co., Led., Tokyo, Japan) and charged with 390 g of 1.3 mm diameter Potters glass beads (Potters Industries, Inc., Parsippany, N.J.). The mill was operated at 2,000 RPM for 4.5 hours without cooling water circulating through the cooling jacket of the milling chamber.

A 12% (w/w) solids toner concentrate exhibited the following properties as determined using the test methods described above:

Volume Mean Particle Size: 2.44 micron
Q/M: 146 μC/g
Bulk Conductivity: 222 picoMhos/cm
Percent Free Phase Conductivity: 2.87%
Dynamic Mobility: 9.90E-11 ($m^2$/Vsec)

Liquid Toner Composition 3

Graft Stabilizer Preparation

Graft Stabilizer Material A

A 5000 ml 3-neck round flask equipped with a condenser, a thermocouple connected to a digital temperature controller, a nitrogen inlet tube connected to a source of dry nitrogen and a magnetic stirrer, was charged with a mixture of 2557 g of Norpar™ 12, 849 g of TCHMA, 26.8 g of 98% HEMA and 13.13 g of V601. While stirring the mixture, the reaction flask was purged with dry nitrogen for 30 minutes at flow rate of approximately 2 liters/minute. A hollow glass stopper was then inserted into the open end of the condenser and the nitrogen flow rate was reduced to approximately 0.5 liters/min. The mixture was heated to 70° C. for 16 hours. The conversion was quantitative.

The mixture was heated to 90° C. and held at that temperature for 1 hour to destroy any residual V601, and then was cooled back to 70° C. The nitrogen inlet tube was then removed, and 13.6 g of 95% DBTDL were added to the mixture, followed by 41.1 g of TMI. The TMI was added drop wise over the course of approximately 5 minutes while stirring the reaction mixture. The nitrogen inlet tube was replaced, the hollow glass stopper in the condenser was removed, and the reaction flask was purged with dry nitrogen for 30 minutes at a flow rate of approximately 2 liters/minute. The hollow glass stopper was reinserted into the open end of the condenser and the nitrogen flow rate was reduced to approximately 0.5 liters/min. The mixture was allowed to react at 70° C. for 6 hours, at which time the conversion was quantitative.

The mixture was then cooled to room temperature. The cooled mixture was a viscous, transparent liquid containing no visible insoluble mater. The percent solids of the liquid mixture was determined to be 29.35% using thermo-gravimetric method described above. Subsequent determination of molecular weight was made using the GPC method described above; the copolymer had a $M_w$ of 341,150 and $M_w/M_n$ of 2.63 based on two independent measurements. The product is a copolymer of TCHMA and HEMA containing random side chains of TMI and is designed herein as TCHMA/HEMA-TMI (97/3-4.7% w/w) and can be used as a dispersant for pigments.

Graft Stabilizer Material B

A 5000 ml 3-neck round flask equipped with a condenser, a thermocouple connected to a digital temperature controller, a nitrogen inlet tube connected to a source of dry nitrogen and a magnetic stirrer, was charged with a mixture of 2557 g of Norpar™ 12, 849 g of TCHMA, 26.8 g of 98% HEMA and 13.13 g of V601. While stirring the mixture, the reaction flask was purged with dry nitrogen for 30 minutes at flow rate of approximately 2 liters/minute. A hollow glass stopper was then inserted into the open end of the condenser and the nitrogen flow rate was reduced to approximately 0.5 liters/min. The mixture was heated to 70° C. for 16 hours. The conversion was quantitative.

The mixture was heated to 90° C. and held at that temperature for 1 hour to destroy any residual V601, and then was cooled back to 70° C. The nitrogen inlet tube was then removed, and 13.6 g of 95% DBTDL were added to the mixture, followed by 41.1 g of TMI. The TMI was added drop wise over the course of approximately 5 minutes while stirring the reaction mixture. The nitrogen inlet tube was replaced, the hollow glass stopper in the condenser was removed, and the reaction flask was purged with dry nitrogen for 30 minutes at a flow rate of approximately 2 liters/minute. The hollow glass stopper was reinserted into the open end of the condenser and the nitrogen flow rate was reduced to approximately 0.5 liters/min. The mixture was allowed to react at 70° C. for 6 hours, at which time the conversion was quantitative.

The mixture was then cooled to room temperature. The cooled mixture was a viscous, transparent liquid containing no visible insoluble mater. The percent solids of the liquid mixture was determined to be 30.45% using thermo-gravimetric method described above. Subsequent determination of molecular weight was made using the GPC method described above; the copolymer had a $M_w$ of 369,600 and $M_w/M_n$ of 2.77 based on two independent measurements. The product is a copolymer of TCHMA and HEMA containing random side chains of TMI and is designed herein as TCHMA/HEMA-TMI (97/3-4.7% w/w) and can be used as a dispersant for pigments.

Organosol Preparation

A 50 gallon reactor, equipped with a condenser, a thermocouple connected to a digital temperature controller, a nitrogen inlet tube connected to a source of dry nitrogen and a mixer, was thoroughly cleaned with a heptane reflux and then thoroughly dried at 100° C. under vacuum. A nitrogen blanket was applied and the reactor was allowed to cool to ambient temperature. The reactor was charged with a mixture of 164 lb of Norpar™ 12 and 8.94 lb of the graft stabilizer mixture obtained by combining the graft stabilizers materials A & B prepared above @ 29.9% polymer solids along with an additional 1 lb of Norpar™ 12 to rinse the container. Agitation was then turned on at a rate of 60 RPM, and temperature was checked to ensure maintenance at ambient. Next, 0.22 lb of V-601 was added, along with 1 lb of Norpar™ 12 to rinse the container. 18.6 lb of EMA was added with another 1 lb Norpar™ 12 for rinsing the container. Finally, 2.8 lb of EA was added with an additional 1 lb of Norpar™ 12 to rinse the container. A full vacuum was then applied for 10 minutes, and then broken by a nitrogen blanket. A second vacuum was pulled for 10 minutes, and then agitation stopped to verify that no bubbles were coming out of the solution. The vacuum was then broken with a nitrogen blanket and a light flow of nitrogen of 1 CFH (cubic foot per hour) was applied. Agitation of 75 RPM was resumed and the temperature of the reactor was heated to 70° C. and maintained for 16 hours. The conversion was quantitative.

Approximately 20 lb of n-heptane and 40 lb of Norpar™ 12 were added to the cooled organosol. The resulting mixture was stripped of residual monomer using a rotary evaporator equipped with a dry ice/acetone condenser. Agitation was held at 90 RPM and the batch heated to 95° C. The nitrogen flow was stopped and a vacuum of 165 mbar was pulled and held for 10 minutes. The vacuum was then increased to 105, 66, and 40 mbar, being held at each level for 10 minutes. Finally, the vacuum was increased to 26 mbar and held for 30 minutes. At that point a full vacuum was pulled and 62 lbs of distillate was collected. The vacuum was then broken, and the stripped organosol was cooled to room temperature, yielding an opaque white dispersion.

This organosol is designed TCHMA/HEMA-TMI//EMA/EA (97/3-4.7//87/13% w/w). The percent solid of the organosol dispersion after stripping was determined as 12.00% using thermo-gravimetric method described above. Subsequent determination of average particles size was made using the light scattering method described above; the organosol had a volume average diameter of 110.5 μm. The glass transition temperature was measured using DSC, as described above. The organosol particles had a $T_g$ of 57.07° C.

Liquid Toner Preparation

This is an example of preparing a yellow liquid toner at a weight ratio of organosol copolymer to pigment (O/P ratio) of 5 using the organosol prepared in example ?, for which the weight ratio of D material to S material was 8. 167 g of the organosol at 12.00% (w/w) solids in Norpar™ 12 were combined with 125 g of Norpar™ 12, 0.6 Pigment Yellow 138, 5.4 g of Pigment Yellow 83 (Sun Chemical Company, Cincinnati, Ohio) and 1.96 g of 6.11% Zirconium HEX-CEM solution (OMG Chemical Company, Cleveland, Ohio) in an 8 ounce glass jar. This mixture was then milled in a 0.5 liter vertical bead mill (Model 6TSG-1/4, Amex Co., Led., Tokyo, Japan) and charged with 390 g of 1.3 mm diameter Potters glass beads (Potters Industries, Inc., Parsippany, N.J.). The mill was operated at 2,000 RPM for 2.48 hours without cooling water circulating through the cooling jacket of the milling chamber.

A 9.25% (w/w) solids toner concentrate exhibited the following properties as determined using the test methods described above:

Volume Mean Particle Size: 2.69 micron

Q/M: 814 μC/g

Bulk Conductivity: 239 picoMhos/cm

Percent Free Phase Conductivity: 1.71%

Dynamic Mobility: 2.01E-10 $(m^2/Vsec)$

Overhead Projection Film Printing

In a series of experiments, the inventors tested a variety of parameters to determine the conditions for printing and fusing electrophotographic images having a range of transparencies when fused onto overhead projection film. For the liquid electrophotographic printing examples which follow, the inventors varied the liquid toner composition as well as the drying time between printing the liquid electrophotographic image and fusing the image to the overhead projection film. In addition, the inventors varied the fusing temperature between 100–155° C. Fusing was accomplished bypassing the liquid electrophotographically printed overhead projection film through a nip created by two heated rubber rollers at a surface speed of 5 inches per second.

Some of the liquid electrophotographic images fused on overhead projection film were subsequently treated with a spray-on wax (Pledge™, S. C. Johnson & Son, Inc., Racine, Wis.) coating in an attempt to improve projected transparency. In addition, exemplary multi-color dry toner electrophotographic images were printed and fused onto overhead projection transparency film using a Hewlett-Packard Laserjet™ 8500 DN (Hewlett-Packard Corp., Boise, Id.). Uncoated polyester film sheets of thickness 0.002 inches were used as the overhead projection film or transparency support for all of the following examples:

For Cyan Transparencies Made with the Cyan Liquid Toner of Composition 1:

| Condition of Making | Transmitted | Scattered | SCORE | Projection |
|---|---|---|---|---|
| Air dry + Fuse @ 155 C. | 7.7 μW | 155 μW | 20.1 | Looks Black |
| Fuse @ 100 C. + Wax | 83 μW | 1485 μW | 17.9 | Looks Black |
| Dry 30 sec Fuse 155 C. | 205 μW | 1000 μW | 5.0 | Almost good |
| Dry 0 sec Fuse 155 C. | 173 μW | 415 μW | 2.4 | Very clear |

For Magenta Transparencies Made with the Magenta Liquid Toner of Composition 2:

| Condition of Making | Transmitted | Scattered | SCORE | Projection |
|---|---|---|---|---|
| Fuse @ 100 C. + Wax | 978 μW | 3800 μW | 3.9 | Almost good |
| Fuse @ 100 C. No Wax | 963 μW | 3338 μW | 3.5 | Almost good |
| Dry 0 sec Fuse @ 155 C. | 1174 μW | 1950 μW | 1.7 | Excellent |
| Dry 20 sec Fuse @ 155 C. | 1000 μW | 3490 μW | 3.5 | Almost good |

For Yellow Transparencies Made with the Yellow Liquid Toner of Composition 3:

| Condition of Making | Transmitted | Scattered | SCORE | Projection |
|---|---|---|---|---|
| Fuse @ 100 C. + Wax | 699 μW | 6125 μW | 8.8 | Deep Gold |
| Dry 0 sec Fuse @ 155 C. | 1290 μW | 1230 μW | 1.0 | Excellent |
| Dry 0 sec Fuse @ 155 C. | 1100 μW | 1980 μW | 1.3 | Excellent |
| Fuse @ 100 C. No Wax | 463 μW | 6577 μW | 14.2 | Looks Black |
| Dry 0 sec Fuse @ 130 C. | 1095 μW | 2388 μW | 2.2 | Excellent |
| Fuse @ 100 C. + Wax | 777 μW | 5650 μW | 7.3 | Gold |
| Dry 2 min Fuse @ 155 C. | 900 μW | 3640 μW | 4.0 | Light Gold |
| Dry 1 min Fuse @ 155 C. | 872 μW | 3590 μW | 4.1 | Light Gold |

For Multicolor Transparencies Made with Dry Toners on the Hewlett-Packard Laserjet™ 8500 DN

| Condition of Making | Transmitted | Scattered | SCORE | Projection |
|---|---|---|---|---|
| Dry Toner Yellow | 197 μW | 12,040 μW | 61 | Muddy Gold |
| Dry Toner Cyan | 3.9 μW | 1440 μW | 369 | Muddy Cyan |
| Dry Toner Magenta | 59 μW | 11,310 μW | 191 | Muddy Magenta |

The light detectors may be any light detection system that can quantify the amount of incident radiation received by the detector. It is possible to use semiconductor, piezoelectric, electro-optic, wide area detectors, fiber optic or other detection systems at the choice of the designer. The inventors used a Model 371 Optical Power Meter (available from United Detector Technology, Baltimore, Md.). The laser light used by the inventors was LaserMax, Inc., Model LAS 200-650-5 (available from LaserMax, Inc. Rochester, N.Y.). One example is a single chip channel GaAs electro-optic waveguide device. The device comprises an input waveguide, into which the beam is input, and a 1 to 16 way multimode interference splitter for splitting the input beam into n different outputs. For example, this may be a multimode interference splitter as described in U.S. Pat. No. 5,410,625. The device also comprises 16 electro-optic waveguides for optical phase control, each electro-optic waveguide may have an electrode for applying an electric field across each waveguide. The system my be self-contained, with transparencies inserted into an apparatus, the apparatus closed against incident radiation and light, measurements taken and recorded and evaluated, and the system opened for removal of that system. Blockage of ambient light is desirable or essential for precise measurements. The ratios of $(\lambda_T)/\lambda_S)$ or $(\lambda_S)/(\lambda_T)$ are highly meaningful and represent clear indicators of the suitability of transparencies, even before they are projected onto a screen. In different uses, different ratios may be acceptable, but the user can determine what values are acceptable or not, or a program associated with a processor receiving the data can evaluate the suitability of the ratio for any use or specific uses. For example, where a small projection is to be used for a small, tightly packed audience in a small room with significant background light, a relatively higher $(\lambda_S/\lambda_T)$ ratio (e.g., 4.0–6.0) may be acceptable. On the other hand, where a very large projection is to be provided in a large dark room where color rendition is significant to the presentation, only a lower $(\lambda_S)/\lambda_T)$ ratio (e.g., 1.0–2.0) may be acceptable.

Although specific examples, materials, values and components have been described in the examples and specification, these numbers, except where so specifically stated, are not intended to be limiting to the scope of the invention.

What is claimed:

1. A method for evaluating the scattering properties of a toned or inked transparency image comprising:
    projecting radiation through the inked or toned transparency image to form a transmitted beam of radiation;
    splitting the transmitted beam of radiation into at least two distinct beams of radiation, a first distinct beam and a second distinct beam;
    measuring a first amount of energy in the first distinct beam that corresponds to non-scattered light;
    measuring a second amount of energy in the second distinct beam that corresponds to scattered light; and
    comparing the first amount of energy to the second amount of energy to determine the proportion of the transmitted beam of radiation that is not scattered to evaluate the scattering properties of the toned or inked transparency image.

2. The method of claim 1 wherein the radiation projected through the transparency image comprises laser radiation.

3. The method of claim 1 wherein the radiation projected through the transparency image comprises laser light.

4. The method of claim 3 wherein the laser light comprises infrared laser light.

5. The method of claim 4 wherein the laser light comprises monochromatic laser light.

6. The method of claim 4 wherein each distinct beam is directed towards different areas of a light detector and each light detector area has a light opaque area and a light transmissive area to distinguish scattered light from non-scattered light.

7. The method of claim 1 wherein the transparency image is formed by no more than two toners, with one of the toners being black.

8. The method of claim 1 wherein the transparency image is formed by one color toner.

9. The method of claim 1 wherein each distinct beam is directed towards different areas of a radiation detector.

10. The method of claim 9 wherein each radiation detector area has a radiation opaque area and a radiation transmissive area to distinguish scattered radiation from non-scattered radiation.

11. The method of claim 1 wherein the ratio of the second amount of energy as $\lambda_2$ to the first amount of energy $\lambda_T$ is not more than 3.0.

12. A system for evaluating the scattering properties of a toned or inked transparency image comprising:
    a radiation source that projects radiation through the toned or inked transparency image to form a transmitted beam of radiation;
    a beam splitter that splits the transmitted beam of radiation into at least two distinct beams of radiation, a first distinct beam and a second distinct beam;
    a radiation detector that measures a first amount of energy in the first distinct beam that corresponds to non-scattered light;
    a radiation detector that measures a second amount of energy in the second distinct beam that corresponds to scattered light; and a processor for comparing the first amount of energy to the second amount of energy to determine the proportion of the transmitted beam of radiation that is not scattered.

13. The system of claim 12 wherein the ratio of the second amount of energy as $\lambda_2$ to the first amount of energy $\lambda_T$ is not more than 3.0.

14. A self-contained unit for evaluating the light scattering properties of a toned or inked transparency image on a support comprising
   a support element for a transparency image on a support layer;
   a radiation source that projects radiation through the toned or inked transparency image to form a transmitted beam of radiation;
   a beam splitter that splits the transmitted beam of radiation into at least two distinct beams of radiation, a first distinct beam and a second distinct beam;
   a radiation detector that measures a first amount of energy in the first distinct beam that corresponds to non-scattered light;
   a radiation detector that measures a second amount of energy in the second distinct beam that corresponds to scattered light; and
   a processor for comparing the first amount of energy to the second amount of energy to determine the proportion of the transmitted beam of radiation that is not scattered.

15. The unit of claim 14 having a comparator that displays acceptability indicated by the processor for the comparison of the first amount and the second amount of energy.

16. The unit of claim 15 wherein the comparison is by an approval/disapproval signal.

17. The unit of claim 16 wherein the comparison is by display of a numeric value.

18. The unit of claim 14 wherein the ratio of the second amount of energy as $\lambda_2$ to the first amount of energy $\lambda_T$ is not more than 3.0.

* * * * *